US007319087B2

(12) United States Patent
Hansen

(10) Patent No.: US 7,319,087 B2
(45) Date of Patent: Jan. 15, 2008

(54) **ANTIMICROBIAL POLYPEPTIDE FROM *ASPERGILLUS NIGER***

(75) Inventor: Morgens Trier Hansen, Lynge (DK)

(73) Assignee: Novozymes A/S, Bagsvaerd (DK)

( * ) Notice: Subject to any disclaimer, the term of this patent is extended or adjusted under 35 U.S.C. 154(b) by 573 days.

(21) Appl. No.: 10/474,647

(22) PCT Filed: May 3, 2002

(86) PCT No.: PCT/DK02/00289

§ 371 (c)(1),
(2), (4) Date: Oct. 9, 2003

(87) PCT Pub. No.: WO02/090384

PCT Pub. Date: Nov. 14, 2002

(65) Prior Publication Data

US 2006/0183675 A1  Aug. 17, 2006

Related U.S. Application Data

(60) Provisional application No. 60/289,102, filed on May 7, 2001.

(30) Foreign Application Priority Data

May 4, 2001  (DK) .............................. 2001 00706

(51) Int. Cl.
*A61K 38/00*  (2006.01)
*C07K 14/00*  (2006.01)
*C07H 21/04*  (2006.01)

(52) U.S. Cl. ..................... 514/2; 530/350; 536/23.1
(58) Field of Classification Search .................. None
See application file for complete search history.

(56) References Cited

FOREIGN PATENT DOCUMENTS

| WO | WO 91/19738 | 12/1991 |
|----|-------------|---------|
| WO | WO 94/01459 | 1/1994 |
| WO | WO 00/32220 | 6/2000 |

OTHER PUBLICATIONS

Bowie, et al., Deciphering the message in the protein sequences: Tolerance to amino acid substitutions (1990) Science, vol. 247, pp. 1306-1310.*
Rudinger, Peptide Hormones, University Park Press, 1976, Baltimore, MD., pp. 1-7.*
Lee et al., Biochemical and Biophysical Research, vol. 263, pp. 646-651 (1999).
Martinez Ruiz et al., Biochemical and Biophysical, vol. 1340, pp. 81-87 (1998).
Tsang et al., *Aspergillus niger*, ID BE759789 (2000).
Nakaya et al., Eur. J. Biochem, vol. 193, pp. 31-38 (1990).
Olivas et al., Biochemistry, vol. 34, pp. 3009-3021 (1995).
Wnendt et al., Nucleic Acids Research, vol. 18, No. 13, p. 3987 (1990).

* cited by examiner

*Primary Examiner*—Robert B. Mondesi
(74) *Attorney, Agent, or Firm*—Michael W. Krenicky

(57) ABSTRACT

The present invention relates to an anti-microbial polypeptide and a DNA construct encoding said anti-microbial polypeptide and the use of said anti-microbial polypeptide.

17 Claims, 2 Drawing Sheets

```
                    (1) 1         10        20        30        40              58
A.niger mature (C-40-1) (1) LSKYGGECSVEHNTCTYLKGGKDHIVSCPSAANLRCKTERHHCEYDEHHKTVDCQTPV
   A.niger(Lee et al.) (1) LSKYGGECSLEHNTCTYRKDGKNHVVSCPSAANLRCKTDRHHCEYDDHHKTVDCQTPV
            Consensus (1) LSKYGGECSLEHNTCTY K GK HIVSCPSAANLRCKTDRHHCEYDDHHKTVDCQTPV
```

```
                      (1) 1         10        20        30        40          58
A.niger mature (C-40-1) (1) LSKYGGECSVEHNTCTYLKGGKDHIVSCPSAANLRCKTERHHCEYDEHHKTVDCQTPV
    A.niger(Lee et al.) (1) LSKYGGECSLEHNTCTYRKDGKNHVVSCPSAANLRCKTDRHHCEYDDHHKTVDCQTPV
             Consensus  (1) LSKYGGECSLEHNTCTY K GK HIVSCPSAANLRCKTDRHHCEYDDHHKTVDCQTPV
```

ANTIMICROBIAL POLYPEPTIDE FROM ASPERGILLUS NIGER

CROSS-REFERENCE TO RELATED APPLICATIONS

This application is a 35 U.S.C. 371 national application of PCT/DK02/00289 filed May 3, 2002, which claims priority or the benefit under 35 U.S.C. 119 of Danish application no. PA 2001 00706 filed May 4, 2001 and U.S. provisional application No. 60/289,102 filed May 7, 2001, the contents of which are fully incorporated herein by reference.

FIELD OF THE INVENTION

The present invention relates to a DNA construct comprising a DNA sequence derived from *Aspergillus niger* encoding an anti-microbial polypeptide, and variants thereof. The invention also relates to the use of said anti-microbial polypeptide for controlling or combating microbial organisms; to a composition comprising the anti-microbial polypeptide of the invention as an active ingredient; to a method of expressing the anti-microbial polypeptide in a host cell; to the use of the anti-microbial polypeptide for the preparation of a composition for the treatment or prophylaxis of microbial organisms for use in, e.g., wound healing composition/products or products such as bandages, medical devices such as, e.g., catheters and further in anti-dandruff hair products.

BACKGROUND OF THE INVENTION

Recently an anti-fungal peptide from *Aspergillus niger* has been isolated by Lee et al. (1999), Biochem. Biophys. Res. Commun. 263, 646-651). The *A. niger* antifungal peptide is reported to inhibit the growth of yeasts including the pathogen *C. albicans*. The Lee et al. reference describes the isolation of the peptide and the determination of the amino acid sequence of the mature peptide. The gene encoding the *A. niger* antifungal peptide was not cloned, and the sequence of the primary translation product remains unknown. It is not known whether the primary product contains signal and pro-peptide sequences, which could be essential to efficient secretion and processing of the product.

Another anti-fungal peptides from *Aspergillus giganteus* (Nakaya, K et al., (1990), Eur. J. Biochem. 19, p. 31-38) has been isolated and characterized. The *A. giganteus* peptide is small (51 amino acids), alkaline (pI 9.3) and contains four S—S interchain bridges (Campos-Olivas, R. et al. (1995), Biochemistry 34, 3009-3021). Other peptides have been isolated from the *Aspergilli A. clavatus* and *A. giganteus* A3274 (WO 94/01459).

SUMMARY OF THE INVENTION

The present invention relates to a DNA construct comprising a DNA sequence encoding a polypeptide with antimicrobial activity and the use of said polypeptide.

In the first aspect the invention relates to a DNA construct comprising a DNA sequence encoding a polypeptide exhibiting anti-microbial activity, which sequence comprises the nucleotide sequence shown in SEQ ID NO: 1 or a DNA sequence being at least 60% identical to the part of SEQ ID NO: 1 encoding the mature anti-microbial peptide, i.e., the coding part of SEQ ID NO: 1 (which is nucleotides 208 to 510), or a fragment thereof.

In the second aspect the present invention relates to a polypeptide exhibiting anti-microbial activity encoded by
i) a DNA sequence of the invention,
or which polypeptide sequence
a) comprises the amino acid sequence shown in SEQ ID NO: 2 (positions 1 to 58), or
b) a fragment and/or variant of the amino acid sequence shown in SEQ ID NO: 2 (positions 1 to 58) exhibiting anti-microbial activity, or
c) a fragment and/or variant as defined in b) which further has an N-terminal extension in comparison to the mature part of SEQ ID NO: 2, i.e., positions 1 to 58.

The term "variant" as used in connection with the antimicrobial polypeptide is intended to indicate a polypeptide which is derived from the polypeptide having the amino acid sequence shown in SEQ ID NO: 2, or a naturally occurring variant. Typically, the variant differs from the native antimicrobial polypeptide by one or more amino acid residues, which may have been added or deleted from either or both of the N-terminal or C-terminal end of the polypeptide, inserted or deleted at one or more sites within the amino acid sequence of the polypeptide, or substituted with one or more amino acid residues within, or at either or both ends of the amino acid sequence of the polypeptide.

Preferably, the anti-microbial polypeptide of the invention comprises the amino acid sequences shown in SEQ ID NO: 2; or allelic variants thereof; or a fragment thereof that has anti-microbial activity.

The term "fragment" of the polypeptide of the invention means a polypeptide, which lacks one or more amino acids in the amino and/or carboxyl terminus of the parent amino acid sequence shown in SEQ ID NO: 2, but retains antimicrobial activity. In other words, a polypeptide fragment of the invention is shorter than the parent polypeptide, in the present case the sequence shown in SEQ ID NO: 2 (positions 1 to 58). The polypeptide fragment of the invention may be protein engineered, e.g., from SEQ ID NO. 2, using any methods known in the art or may also be a natural polypeptide with anti-microbial activity derived from a microorganism being shorter (i.e., consisting of fewer amino acids) than the polypeptide shown in SEQ ID NO: 2. The anti-microbial polypeptide of the invention may also be prepared synthetically. The polypeptide fragment of the invention may be from 1 to 10 amino acids shorter in the N- and/or C-terminal in comparison to the above mentioned parent polypeptide shown in SEQ ID NO: 2, preferably from 1 to 7 amino acids residues, especially from 1-5 amino acid residues.

An allelic variant denotes any of two or more alternative forms of a gene occupying the same chromosomal locus, i.e., sequence homology between the two variants extends beyond the gene and its control sequences.

Allelic variation arises naturally through mutation, and may result in polymorphism within populations.

Gene mutations can be silent (no change in the encoded polypeptide) or may encode polypeptides having altered amino acid sequences. An allelic variant of a polypeptide is a polypeptide encoded by an allelic variant of a gene.

The amino acid sequences of homologous anti-microbial polypeptides may differ from the amino acid sequence shown in SEQ ID NO: 2 by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 1-15 amino acids;

small amino- or carboxyl-terminal extensions, such as an amino-terminal Methionine residue; or small extensions of up to about 20-25 residues that, e.g., facilitates purification by changing net charge or another function, such as a poly-histidine tract, an antigenic epitope or a binding domain.

In the present context, the three-letter code of the amino acids has been used in its conventional meaning. Unless indicated explicitly, the amino acids mentioned herein are L-amino acids.

The *A. niger* ORF encodes a primary translated product which can be divided into the following functional parts: A 18 amino acids signal peptide, a 16 amino acids pro-peptide and a 58 amino acid mature polypeptide with anti-microbial activity.

The anti-microbial peptides of the invention are synthesized as prepro-peptides, i.e., in addition to a signal peptide the gene encodes a pro-peptide, which is matured (processed) into the active mature anti-microbial peptides.

In addition to complications seen in connected with production of most other polypeptides, production of anti-microbial peptide have a further complication in that the produced anti-microbial product may inhibit or even kill its host cell used for the production. This is often seen as a problem in connection with especially heterologous production.

In a third aspect, the present invention relates to a recombinant expression vector comprising a DNA construct of the invention.

In a fourth aspect the invention related to a host cell comprising the expression vector of the invention, in particular a cell of the filamentous fungus genus *Aspergillus*, in particular of the group *Aspergillus Nigri*, especially the species *A. niger* or the group *Aspergillus Flavus*, especially the species *A. oryzae*, or the bacterial genus *Bacillus*.

The present invention also relates to a method of producing an anti-microbial polypeptide of the invention, in particular comprising the amino acid sequence shown in SEQ ID NO: 2, or a fragment or a variant thereof exhibiting anti-microbial activity, which method comprises
(a) inserting a DNA construct encoding the polypeptide into a suitable expression vector,
(b) transforming a suitable host cell with the recombinant expression vector of step (a),
(c) culturing the transformed host cell in a suitable culture medium under conditions conducive to the production of the polypeptide, and
(d) recovering the polypeptide from the host cell or culture medium obtained in step (c).

The invention also relates to a method of producing an anti-microbial polypeptide of the invention, comprising cultivating a micro-organism which, in nature, is capable of producing the polypeptide on a suitable culture medium and under conditions allowing the production of the polypeptide, and recovering the polypeptide from the resulting biomass and/or fermented culture medium.

The invention also relates to a method for homologously or recombinantly producing a polypeptide having anti-microbial activity of the invention comprising (a) cultivating the host cell of the invention under conditions conducive to expression of the polypeptide; and (b) recovering the polypeptide.

The invention also relates to a composition comprising, as an active ingredient, an anti-microbial polypeptide of the invention, which further may comprise an additional biocidal agent.

The invention also relates to the use of an anti-microbial polypeptide of the invention for controlling or combating micro-organisms, such as fungal organisms or bacteria.

The composition and anti-microbial agent the invention may be used as an anti-microbial veterinarian or human therapeutic or prophylactic agent. Thus, the composition and anti-microbial polypeptide of the invention may be used in the preparation of a veterinarian or human therapeutic agent for the treatment of a microbial, such as fungal infection, or for prophylactic treatment.

Finally the invention relates to wound healing composition or products such as bandages, medical devices such as, e.g., catheters and further to anti-dandruff hair products, such as a shampoo.

BRIEF DESCRIPTION OF THE FIGURES

FIG. 1 shows an alignment of the amino acid sequence (SEQ ID NO: 11) of an *A. niger* anti-fungal polypeptide determined by Lee et al., (1999), Biochem. Biophys. Res. Commun. 263, 646-652, the deduced amino acid sequences (SEQ ID NO: 10) for the mature anti-fungal polypeptide from *A. niger* (strain C-40-1), and the consensus sequence (SEQ ID NO: 12) deduced there from.

DETAILED DESCRIPTION OF THE INVENTION

DNA Sequence Encoding an Anti-Microbial Polypeptide

Figure 2:
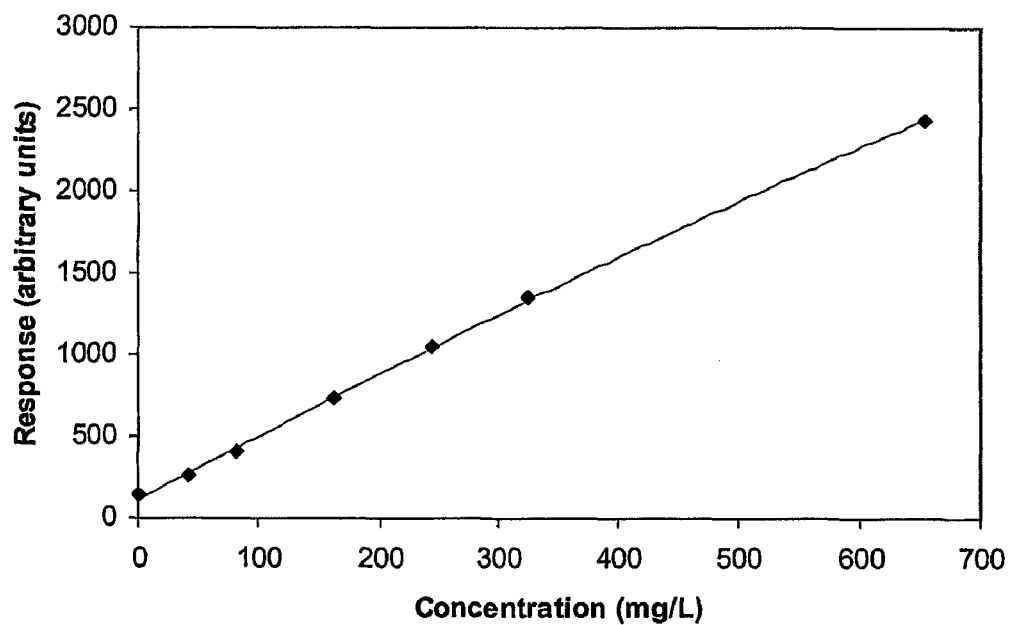
FIG. 2 shows the Standard curve for the LC-MS measurements of *Aspergillus niger* AMP.

In the first aspect the present invention relates to a DNA construct (nucleic acid construct) comprising a DNA sequence encoding a polypeptide exhibiting anti-microbial activity, such as anti-fungal activity, which sequence comprises the nucleotide sequence shown in SEQ ID NO: 1 or a DNA sequence being at least 60% identical to the part of SEQ ID NO: 1 encoding the mature anti-microbial peptide, i.e., the coding part of SEQ ID NO: 1 (which is nucleotides 208 to 510), or a fragment thereof.

The terms "nucleic acid construct/sequence" and "DNA construct/sequence" is used interchangeable in this application.

The term "DNA construct" (or "nucleic acid construct") is defined herein as a nucleic acid molecule, either single- or double-stranded, which is isolated from naturally occurring gene(s), which has been modified to contain segments of nucleic acid, which are combined and juxtaposed in a manner, which would not otherwise exist in nature. The term nucleic acid construct may be synonymous with the term expression cassette when the nucleic acid construct contains all the control sequences required for expression of anti-microbial polypeptide of the invention.

The term "coding sequence" as defined herein refer to the sequence, which is transcribed into mRNA and translated into a polypeptide comprising the amino acid sequence which exhibits anti-microbial activity of the invention when placed under the control of the below mentioned control sequences.

The boundaries of the coding sequence are generally determined by a translation start codon ATG at the 5'-terminus and a translation stop codon at the 3'-terminus. A coding sequence can include, but is not limited to, DNA, cDNA, and recombinant nucleic acid sequences.

An isolated nucleic acid sequence encoding an anti-microbial polypeptide of the invention may be manipulated in a variety of ways to provide for increased expression. Manipulation of the nucleic acid sequence encoding a polypeptide with anti-microbial activity prior to its insertion into a vector may be desirable or necessary depending on the expression vector. The techniques for modifying nucleic acid sequences utilizing cloning methods are well known in the art.

The term "anti-microbial polypeptide" as used herein is intended to comprise the linear as well as the active folded structures of the polypeptide, and may, where appropriate, be used interchangeably with the term "anti-microbial protein".

The term "anti-microbial activity" means in the context of the present invention that the polypeptide encoded by the DNA sequence of the invention is active in controlling or combating microbial organisms, including fungal organisms, such as yeasts and/or filamentous fungus, and/or bacterial organisms. Suitable assays for assessing whether a polypeptide has anti-microbial activity include the one described by Lacadena, J. et al. (1995), Archives of Biochemisty and Biophysics 324 (273-281) and the ones described in the "Materials & Methods" section as Bioassay I.

The DNA construct comprises the DNA sequence shown in SEQ ID NO: 1, in particular the polypeptide encoding part of SEQ ID NO: 1, or a DNA sequence being at least 60%, such as at least 70%, preferably at least 80%, even more preferably at least 90%, even more preferably at least 95%, even more preferred at least 97%, especially at least 99% identical to SEQ ID NO: 1, in particular the polypeptide coding part, which may be operably linked to one or more control sequences capable of directing the expression of the coding sequences in a suitable host cell under conditions compatible with the control sequences.

The term "identity" (homology) used in the context of the present invention may be determined as the degree of identity between the two sequences indicating a derivation of the first sequence from the second. The identity may suitably be determined by means of computer programs known in the art such as GAP provided in the GCG program package. Thus, Gap GCGv8 may be used with the following default parameters: GAP creation penalty of 5.0 and GAP extension penalty of 0.3, default scoring matrix, for nucleic sequences and 3.0 and 0.1, respectively, from polypeptide sequences. GAP uses the method of Needleman/Wunsch/Sellers to make alignments.

A structural alignment between an anti-microbial sequence and another sequence may be used to identify equivalent/corresponding positions in other polypeptides. One method of obtaining said structural alignment is to use the Pile Up programme from the GCG package using default values of gap penalties, i.e., a gap creation penalty of 3.0 and gap extension penalty of 0.1. Other structural alignment methods include the hydrophobic cluster analysis (Gaboriaud et al., (1987), FEBS LETTERS 224, pp. 149-155) and reverse threading (Huber, T; Torda, A E, PROTEIN SCIENCE Vol. 7, No. 1 pp. 142-149 (1998).

The Polypeptide Exhibiting Anti-Microbial Activity

In the second aspect the invention relates to a polypeptide exhibiting anti-microbial activity encoded by
i) a DNA sequence of the invention,
or which polypeptide sequence
  a) comprises the amino acid sequence shown in SEQ ID NO: 2 (positions 1 to 58), or
  b) a fragment and/or variant of the amino acid sequence shown in SEQ ID NO: 2 (positions 1 to 58) exhibiting anti-microbial activity, or
  c) a fragment and/or variant as defined in b) which further has an N-terminal extension in comparison to the mature part of SEQ ID NO: 2 (positions 1 to 58).

N-Terminal Extension

An N-terminal extension may suitably consist of from 1 to 50 amino acids, preferably 2-20 amino acids, especially 3-15 amino acids. In one embodiment N-terminal peptide extension does not contain an Arg (R). In another embodiment the N-terminal extension comprises a kex2 or kex2-like cleavage site as will be defined further below. In a preferred embodiment the N-terminal extension is a peptide, comprising at least two Glu (E) and/or Asp (D) amino acid residues, such as an N-terminal extension comprising one of the following sequences: EAE, EE, DE, DD.

Kex2 Sites

Kex2 sites (see, e.g., Methods in Enzymology Vol 185, ed. D. Goeddel, Academic Press Inc. (1990), San Diego, Calif., "Gene Expression Technology") and kex2-like sites are di-basic recognition sites (i.e., cleavage sites) found between the pro-peptide encoding region and the mature region of some proteins.

Insertion of a kex2 site or a kex2-like site have in certain cases been shown to improve correct endopeptidase processing at the pro-peptide cleavage site resulting in increased protein secretion levels.

In the context of the invention insertion of a kex2 or kex2-like site result in the possibility to obtain cleavage at a certain position in the N-terminal extension resulting in an anti-microbial polypeptide being extended in comparison to the mature polypeptide shown in SEQ ID NO: 2 (positions 1 to 58).

In one preferred embodiment the invention relates to an anti-microbial polypeptide produced by the method of the invention.

Expression Vector and Host Cell of the Invention

The invention also relates to a recombinant expression vector comprising a DNA construct of the invention and a host cell comprising a DNA construct of the invention.

Host Cells

The host cell of the invention, either comprising a DNA construct or an expression vector of the invention is advantageously used as a host cell in the recombinant production of an anti-microbial polypeptide of the invention. The cell may be transformed with the DNA construct of the invention encoding the polypeptide in question, conveniently by integrating the DNA construct (in one or more copies) in the host chromosome. This integration is generally considered to be an advantage as the DNA sequence is more likely to be stably maintained in the cell. Integration of the DNA constructs into the host chromosome may be performed according to conventional methods, e.g., by homologous or heterologous recombination. Alternatively, the cell may be transformed with an expression vector as described above in connection with the different types of host cells.

The cell of the invention may be a cell of a higher organism such as a mammal, an insect or a plant, but is preferably a microbial cell, e.g., a bacterial or a fungal (including yeast) cell.

Eukaryote Host Cells

The host cell may be a eukaryote, such as a mammalian cell, an insect cell, a plant cell or a fungal cell. Useful mammalian cells include Chinese hamster ovary (CHO) cells, HeLa cells, baby hamster kidney (BHK) cells, COS cells, or any number of other immortalized cell lines available, e.g., from the American Type Culture Collection.

In a preferred embodiment, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi,* 8th edition, 1995, CAB International, University Press, Cambridge, UK) as well as the Oomycota (as cited in Hawksworth et al., 1995, In, *Ainsworth and Bisby's Dictionary of The Fungi,* 8th edition, 1995, CAB International, University Press, Cambridge, UK, page 171) and all mitosporic fungi (Hawksworth et al., 1995, supra). Representative groups of Ascomycota include, e.g., *Neurospora, Eupenicillium* (=*Penicillium*), *Emericella* (=*Aspergillus*), *Eurotium* (=*Aspergillus*), and the true yeasts listed below. Examples of Basidiomycota include mushrooms, rusts, and smuts. Representative groups of Chytridiomycota include, e.g., *Allomyces, Blastocladiella, Coelomomyces,* and aquatic fungi. Representative groups of Oomycota include, e.g., *Saprolegniomycetous* aquatic fungi (water molds) such as *Achlya*. Examples of mitosporic fungi include *Aspergillus, Penicillium, Candida,* and *Alternaria*. Representative groups of Zygomycota include, e.g., *Rhizopus* and *Mucor*.

In a preferred embodiment, the fungal host cell is a yeast cell. "Yeast" as used herein includes ascosporogenous yeast (*Endomycetales*), basidiosporogenous yeast, and yeast belonging to the Fungi Imperfecti (*Blastomycetes*). The ascosporogenous yeasts are divided into the families Spermophthoraceae and Saccharomycetaceae. The latter is comprised of four subfamilies, Schizosaccharomycoideae (e.g., genus *Schizosaccharomyces*), Nadsonioideae, Lipomycoideae, and Saccharomycoideae (e.g., genera *Pichia, Kluyveromyces* and *Saccharomyces*). The basidiosporogenous yeasts include the genera *Leucosporidim, Rhodosporidium, Sporidiobolus, Filobasidium,* and *Filobasidiella*. Yeasts belonging to the Fungi Imperfecti are divided into two families, Sporobolomycetaceae (e.g., genera *Sorobolomyces* and *Bullera*) and Cryptococcaceae (e.g., genus *Candida*). Since the classification of yeast may change in the future, for the purposes of this invention, yeast shall be defined as described in *Biology and Activities of Yeast* (Skinner, F. A., Passmore, S. M., and Davenport, R. R., eds, Soc. App. Bacteriol. Symposium Series No. 9, 1980. The biology of yeast and manipulation of yeast genetics are well known in the art (see, e.g., *Biochemistry and Genetics of Yeast,* Bacil, M., Horecker, B. J., and Stopani, A. O. M., editors, 2nd edition, 1987; *The Yeasts,* Rose, A. H., and Harrison, J. S., editors, 2nd edition, 1987; and *The Molecular Biology of the Yeast Saccharomyces,* Strathern et al., editors, 1981).

In a more preferred embodiment, the yeast host cell is a cell of a species of *Candida, Kluyveromyces, Saccharomyces, Schizosaccharomyces, Pichia,* or *Yarrowia*. In a most preferred embodiment, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In a preferred embodiment, the fungal host cell is a filamentous fungal cell. "Filamentous fungi" include all filamentous forms of the subdivision Eumycota and Oomycota (as defined by Hawksworth et al., In, *Ainsworth and Bisby's Dictionary of The Fungi,* 8th edition, 1995, CAB International, University Press, Cambridge, UK. The filamentous fungi are characterized by a vegetative mycelium composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative. In a more preferred embodiment, the filamentous fungal host cell is a cell of a species of, but not limited to, *Acremonium, Aspergillus, Fusarium, Humicola, Mucor, Myceliophthora, Neurospora, Penicillium, Thielavia, Tolypocladium,* and *Trichoderma* or a teleomorph or synonym thereof. In an even more preferred embodiment, the filamentous fungal host cell is an *Aspergillus* cell, preferably one within the groups of *Aspergillus Nigri,* including *A. niger,* and *Aspergillus Flavus,* including *Asperigllus oryzae,* as defined by Raper and Fennell, (1965), pp. 71. In another even more preferred embodiment, the filamentous fungal host cell is an *Acremonium* cell. In another even more preferred embodiment, the filamentous fungal host cell is a *Fusarium* cell. In another even more preferred embodiment, the filamentous fungal host cell is a *Humicola* cell. In another even more preferred embodiment, the filamentous fungal host cell is a *Mucor* cell. In another even more preferred embodiment, the filamentous fungal host cell is a *Myceliophthora* cell. In another even more preferred embodiment, the filamentous fungal host cell is a *Neurospora* cell. In another even more preferred embodiment, the filamentous fungal host cell is a *Penicillium* cell. In another even more preferred embodiment, the filamentous fungal host cell is a *Thielavia* cell. In another even more preferred embodiment, the filamentous fungal host cell is a *Tolypocladium* cell. In another even more preferred embodiment, the filamentous fungal host cell is a *Trichoderma* cell. In a most preferred embodiment the filamentous fungal host cell is within the *Aspergillus* group *A. Nigri* (including *Aspergillus awamori, Aspergillus foetidus, Aspergillus japonicus, Aspergillus niger*) or the *A. Flavus* group including *Aspergillus oryzae*. In another most preferred embodiment, the filamentous fungal host cell is a *Fusarium* cell of the section Discolor (also known as the section *Fusarium*). For example, the filamentous fungal parent cell may be a *Fusarium bactridioides, Fusarium cerealis, Fusarium crookwellense, Fusarium culmorum, Fusarium graminearum, Fusarium graminum, Fusarium heterosporum, Fusarium negundi, Fusarium reticulatum, Fusarium roseum, Fusarium sambucinum, Fusarium sarcochroum, Fusarium sulphureum,* or *Fusarium trichothecioides* cell. In another prefered embodiment, the filamentous fungal parent cell is a *Fusarium* strain of the section Elegans, e.g., *Fusarium oxysporum*. In another most preferred embodiment, the filamentous fungal host cell is a *Humicola insolens* or *Humicola lanuginosa* cell. In another most preferred embodiment, the filamentous fungal host cell is a *Mucor miehei* cell. In another most preferred embodiment, the filamentous fungal host cell is a *Myceliophthora thermophilum* cell. In another most preferred embodiment, the filamentous fungal host cell is a *Neurospora crassa* cell. In another most preferred embodiment, the filamentous fungal host cell is a *Penicillium purpurogenum* cell. In another most preferred embodiment, the filamentous fungal host cell is a *Thielavia terrestris* cell. In another most preferred embodiment, the *Trichoderma* cell is a *Tricho-*

*derma harzianum, Trichoderma koningii, Trichoderma longibrachiatum, Trichoderma reesei* or *Trichoderma viride* cell.

In a preferred embodiment of the invention the host cell is a protease deficient or protease minus strain.

This may for be the protease deficient strain *Aspergillus oryzae* JaL 125 having the alkaline protease gene named "alp" deleted. This strain is described in WO 97/35956 (Novozymes), or EP patent no. 429,490, or the TPAP free host cell, in particular a strain of *A. niger*, disclosed in WO 96/14404.

Transformation of Eukaryote Host Cells

Fungal cells may be transformed by a process involving protoplast formation, transformation of the protoplasts, and regeneration of the cell wall in a manner known per se. Suitable procedures for transformation of *Aspergillus* host cells are described in EP 238 023, EP 184,438, and Yelton et al., 1984, *Proceedings of the National Academy of Sciences USA* 81:1470-1474. A suitable method of transforming *Fusarium* species is described by Malardier et al., 1989, *Gene* 78:147-156 or in copending U.S. Ser. No. 08/269,449. Yeast may be transformed using the procedures described by Becker and Guarente, In Abelson, J. N. and Simon, M. I., editors, *Guide to Yeast Genetics and Molecular Biology*, Methods in Enzymology, Volume 194, pp 182-187, Academic Press, Inc., New York; Ito et al., 1983, *Journal of Bacteriology* 153:163; and Hinnen et al., 1978, *Proceedings of the National Academy of Sciences USA* 75:1920. Mammalian cells may be transformed by direct uptake using the calcium phosphate precipitation method of Graham and Van der Eb (1978, *Virology* 52:546).

Prokaryote Host Cells

The microbial host cell may be a unicellular microorganism, e.g., a prokaryote, or a non-unicellular microorganism, e.g., a eukaryote. Useful unicellular cells are bacterial cells such as gram positive bacteria including, but not limited to, a *Bacillus* cell, e.g., *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis*, and *Bacillus thuringiensis*; or a *Streptomyces* cell, e.g., *Streptomyces lividans* or *Streptomyces murinus*, or gram negative bacteria such as *E. coli* and *Pseudomonas* sp. In a preferred embodiment, the bacterial host cell is a *Bacillus lentus, Bacillus licheniformis, Bacillus stearothermophilus* or *Bacillus subtilis* cell.

Transformation of Prokaryote Host Cells

The transformation of a bacterial host cell may, for instance, be effected by protoplast transformation (see, e.g., Chang and Cohen, 1979, *Molecular General Genetics* 168: 111-115), by using competent cells (see, e.g., Young and Spizizin, 1961, *Journal of Bacteriology* 81:823-829, or Dubnar and Davidoff-Abelson, 1971, *Journal of Molecular Biology* 56:209-221), by electroporation (see, e.g., Shigekawa and Dower, 1988, *Biotechniques* 6:742-751), or by conjugation (see, e.g., Koehler and Thorne, 1987, *Journal of Bacteriology* 169:5771-5278).

Plants

The present invention also relates to a transgenic plant, plant part, or plant cell, which has been transformed with a gene so as to express an anti-microbial polypeptide of the invention in recoverable quantities. The anti-microbial polypeptide in question may be recovered from the plant or plant part. Alternatively, the plant or plant part containing the recombinant anti-microbial polypeptide in question may be used directly for the intended use.

The transgenic plant can be dicotyledonous (a dicot) or monocotyledonous (a monocot).

Examples of monocot plants are grasses, such as meadow grass (blue grass, *Poa*), forage grass such as *festuca, lolium*, temperate grass, such as Agrostis, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rapeseed, and the closely related model organism *Arabidopsis thaliana*.

Examples of plant parts are stem, callus, leaves, root, fruits, seeds, and tubers. Also specific plant tissues, such as chloroplast, apoplast, mitochondria, vacuole, peroxisomes, and cytoplasm are considered to be a plant part. Furthermore, any plant cell, whatever the tissue origin, is considered to be a plant part.

Also included within the scope of the present invention are the progeny of such plants, plant parts and plant cells.

The transgenic plant or plant cell expressing an anti-microbial polypeptide may be constructed in accordance with methods known in the art. Briefly, the plant or plant cell is constructed by incorporating one or more expression constructs comprising a gene encoding an anti-microbial polypeptide into the plant host genome and propagating the resulting modified plant or plant cell into a transgenic plant or plant cell.

Conveniently, the expression construct is a nucleic acid construct, which comprises a nucleic acid sequence encoding an antimicrobial polypeptide operably linked with appropriate regulatory sequences required for expression of the nucleic acid sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences are determined, for example, on the basis of when, where, and how the polypeptide is desired to be expressed. For instance, the expression of the anti-microbial polypeptide in question may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV promoter may be used (Franck et al., 1980, *Cell* 21: 285-294). Organ-specific promoters may be, for example, a promoter from storage sink tissues such as seeds, potato tubers, and fruits (Edwards & Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant and Cell Physiology* 39: 885-889, a *Vicia faba* promoter from the legumin B4 and the unknown seed protein gene from *Vicia faba* (Conrad et al., 1998, *Journal of Plant Physiology* 152: 708-711), a promoter from a seed oil body protein (Chen et al., 1998, Plant and Cell Physiology 39: 935-941, the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991-1000, the *chlorella* virus adenine methyltransferase gene promoter (Mitra and Higgins, 1994, *Plant Molecular Biology* 26: 85-93, or the aldP gene promoter from rice (Kagaya et al., 1995, *Molecular and General Genetics* 248: 668-674), or a wound inducible promoter such as the potato pin2 promoter (Xu et al., 1993, Plant Molecular Biology 22: 573-588.

The selectable marker gene and any other parts of the expression construct may be chosen from those available in the art.

Transformation of Plants

The nucleic acid construct of the invention is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15-38). However it can also be used for transforming monocots, although other transformation methods are generally preferred for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275-281; Shimamoto, 1994, *Current Opinion Biotechnology* 5: 158-162; Vasil et al., 1992, *Bio/Technology* 10: 667-674). An alternative method for transformation of monocots is based on protoplast transformation as described by Omirulleh et al., 1993, *Plant Molecular Biology* 21: 415-428.

Following transformation, the transformants having incorporated therein the expression construct are selected and regenerated into whole plants according to methods well known in the art.

The present invention also relates to methods for producing anti-microbial polypeptides comprising (a) cultivating a transgenic plant or a plant cell comprising a nucleic acid sequence encoding the anti-microbial polypeptide in question under conditions conducive for production of the anti-microbial polypeptide in question; and (b) recovering the polypeptide in question.

Control Sequences

The term "control sequences" is defined herein to include all components, which are necessary or advantageous for expression of the coding sequence of the nucleic acid sequence of the invention. Each control sequence may be native or foreign to the nucleic acid sequence encoding the polypeptide in question. Such control sequences include, but are not limited to, a leader, a polyadenylation sequence, a propeptide sequence, a promoter, a signal sequence, and a transcription terminator. At a minimum, the control sequences include a promoter, and transcriptional and translational stop signals. The control sequences may be provided with linkers, e.g., for the purpose of introducing specific restriction sites facilitating ligation of the control sequences with the coding region of the nucleic acid sequence encoding a polypeptide.

Promoters

The control sequence may be an appropriate promoter sequence, a nucleic acid sequence, which is recognized by a host cell for expression of the nucleic acid sequence. The promoter sequence contains transcription and translation control sequences, which mediate the expression of the polypeptide in question. The promoter may be any nucleic acid sequence, which shows transcriptional activity in the host cell of choice and may be obtained from genes encoding extracellular or intracellular polypeptides either homologous or heterologous to the host cell.

Bacterial Promoters

Examples of suitable promoters for directing the transcription of the nucleic acid constructs of the present invention, especially in a bacterial host cell, are the promoters obtained from the *E. coli* lac operon, the *Streptomyces coelicolor* agarase gene (dagA), the *Bacillus subtilis* levansucrase gene (sacB), the *Bacillus licheniformis* alpha-amylase gene (amyL), the *Bacillus stearothermophilus* maltogenic amylase gene (amyM), the *Bacillus amyloliquefaciens* alpha-amylase gene (amyQ), the *Bacillus licheniformis* penicillinase gene (penP), the *Bacillus subtilis* xylA and xylB genes, and the prokaryotic beta-lactamase gene (Villa-Kamaroff et al., 1978, *Proceedings of the National Academy of Sciences USA* 75:3727-3731), as well as the tac promoter (DeBoer et al., 1983, *Proceedings of the National Academy of Sciences USA* 80:21-25). Further promoters are described in "Useful proteins from recombinant bacteria" in *Scientific American*, 1980, 242:74-94; and in J. Sambrook, E. F. Fritsch, and T. Maniatis, 1989, Molecular Cloning, A Laboratory Manual, 2d edition, Cold Spring Harbor, N.Y.).

Fungal Promoters

Examples of suitable promoters for directing the transcription of the nucleic acid constructs of the present invention in a filamentous fungal host cell are promoters obtained from the genes encoding *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus nidulans* triose phosphate isomerase, *Aspergillus oryzae* alkaline protease, *Aspergillus oryzae* triose phosphate isomerase, *Aspergillus nidulans* acetamidase, *Fusarium oxysporum* trypsin-like protease (as described in U.S. Pat. No. 4,288,627, which is incorporated herein by reference), and hybrids thereof. Particularly preferred promoters for use in filamentous fungal host cells are the TAKA amylase, NA2-tpi (a hybrid of the promoters from the genes encoding *Aspergillus niger* neutral alpha-amylase and *Aspergillus nidulans* triose phosphate isomerase), and glaA promoters.

Yeast Promoters

In a yeast host, useful promoters are obtained from the *Saccharomyces cerevisiae* enolase (ENO-1) gene, the *Saccharomyces cerevisiae* galactokinase gene (GAL1), the *Saccharomyces cerevisiae* alcohol dehydrogenase/glyceraldehyde-3-phosphate dehydrogenase genes (ADH2/GAP), and the *Saccharomyces cerevisiae* 3-phosphoglycerate kinase gene. Other useful promoters for yeast host cells are described by Romanos et al., 1992, *Yeast* 8:423-488.

Transcription Terminators

The control sequence may also be a suitable transcription terminator sequence, a sequence recognized by a host cell to terminate transcription. The terminator sequence is operably linked to the 3' terminus of the nucleic acid sequence encoding the polypeptide. Any terminator, which is functional in the host cell of choice, may be used in the present invention.

Fungal Terminators

Preferred terminators for filamentous fungal host cells are obtained from the genes encoding *Aspergillus niger* neutral alpha-amylase, *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Yeast Terminators

Preferred terminators for yeast host cells are obtained from the genes encoding *Saccharomyces cerevisiae* enolase, *Saccharomyces cerevisiae* cytochrome C (CYC1), or *Saccharomyces cerevisiae* glyceraldehyde-3-phosphate dehydrogenase. Other useful terminators for yeast host cells are described by Romanos et al., 1992, *Yeast* 8:423-488. Terminator sequences are well known in the art for mammalian host cells.

Leader Sequences

The control sequence may also be a suitable leader sequence, a non-translated region of mRNA, which is important for translation by the host cell. The leader sequence is operably linked to the 5' terminus of the nucleic acid sequence encoding the polypeptide. Any leader sequence, which is functional in the host cell of choice, may be used in the present invention.

Fungus Leader Sequences

Preferred leaders for filamentous fungal host cells are obtained from the genes encoding *Aspergillus oryzae* TAKA amylase and *Aspergillus oryzae* triose phosphate isomerase and combinations thereof.

Yeast Leader Sequences

Suitable leaders for yeast host cells are obtained from the *Saccharomyces cerevisiae* enolase (ENO-1) gene, the *Saccharomyces cerevisiae* 3-phosphoglycerate kinase gene, the *Saccharomyces cerevisiae* alpha-factor, and the *Saccharomyces cerevisiae* alcohol dehydrogenase/glyceraldehyde-3-phosphate dehydrogenase genes (ADH2/GAP).

Polyadenylation Sequences

The control sequence may also be a polyadenylation sequence, a sequence which is operably linked to the 3' terminus of the nucleic acid sequence and which, when transcribed, is recognized by the host cell as a signal to add polyadenosine residues to transcribed mRNA. Any polyadenylation sequence, which is functional in the host cell of choice, may be used in the present invention.

Fungus Polyadenylation Sequences

Preferred polyadenylation sequences for filamentous fungal host cells are obtained from the genes encoding *Aspergillus oryzae* TAKA amylase, *Aspergillus niger* glucoamylase, *Aspergillus nidulans* anthranilate synthase, and *Aspergillus niger* alpha-glucosidase.

Yeast Polyadenylation Sequences

Useful polyadenylation sequences for yeast host cells are described by Guo and Sherman, 1995, *Molecular Cellular Biology* 15:5983-5990. Polyadenylation sequences are well known in the art for mammalian host cells.

Signal Peptide

The control sequence may also be a signal peptide-coding region, which codes for an amino acid sequence linked to the amino terminus of the protein, which can direct the expressed protein into the cell's secretory pathway. The 5' end of the coding sequence of the nucleic acid sequence may inherently contain a signal peptide-coding region naturally linked in translation reading frame with the segment of the coding region, which encodes the secreted protein. Alternatively, the 5' end of the coding sequence may contain a signal peptide-coding region, which is foreign to that portion of the coding sequence, which encodes the secreted protein. The foreign signal peptide-coding region may be required where the coding sequence does not normally contain a signal peptide-coding region. Alternatively, the foreign signal peptide-coding region may simply replace the natural signal peptide-coding region in order to obtain enhanced secretion of the protein(s) relative to the natural signal peptide-coding region normally associated with the coding sequence. The signal peptide-coding region may be obtained from a glucoamylase or an amylase gene from an *Aspergillus* species, a lipase or proteinase gene from a *Rhizomucor* species, the gene for the alpha-factor from *Saccharomyces cerevisiae*, an amylase or a protease gene from a *Bacillus* species, or the calf preprochymosin gene. However, any signal peptide-coding region capable of directing the expressed protein into the secretory pathway of a host cell of choice may be used in the present invention.

Bacterial Signal Peptide Sequences

An effective signal peptide-coding region for bacterial host cells is the signal peptide-coding region obtained from the maltogenic amylase gene from *Bacillus* NCIB 11837, the *Bacillus stearothermophilus* alpha-amylase gene, the *Bacillus licheniformis* subtilisin gene, the *Bacillus licheniformis* beta-lactamase gene, the *Bacillus stearothermophilus* neutral proteases genes (nprT, nprS, nprM), and the *Bacillus subtilis* PrsA gene. Further signal peptides are described by Simonen and Palva, 1993, *Microbiological Reviews* 57:109-137.

Fungal Signal Peptide Sequences

An effective signal peptide coding region for filamentous fungal host cells is the signal peptide coding region obtained from *Aspergillus oryzae* TAKA amylase gene, *Aspergillus niger* neutral amylase gene, the *Rhizomucor miehei* aspartic proteinase gene, the *Humicola lanuginosa* cellulase gene, the *Candida antactica* lipase B gene or the *Rhizomucor miehei* lipase gene.

Yeast Signal Peptide Sequences

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, Yeast 8:423-488.

Propeptide Sequences

The control sequence may also be a propeptide coding region, which codes for an amino acid sequence positioned at the amino terminus of a protein. The resultant protein is known as a proenzyme or propolypeptide (or a zymogen in some cases). A propolypeptide is often inactive and can be converted to mature active polypeptide by catalytic or autocatalytic cleavage of the propeptide from the propolypeptide. The propeptide coding region may be obtained from the *Bacillus subtilis* alkaline protease gene (aprE), the *Bacillus subtilis* neutral protease gene (nprT), the *Saccharomyces cerevisiae* alpha-factor gene, the *Candida antactica* lipase B gene, or the *Myceliophthora thermophilum* laccase gene (WO 95/33836).

The nucleic acid constructs of the present invention may also comprise one or more nucleic acid sequences, which encode one or more factors that are advantageous in the expression of the polypeptide, e.g., an activator (e.g., a trans-acting factor), a chaperone, and a processing protease. Any factor that is functional in the host cell of choice may be used in the present invention. The nucleic acids encoding one or more of these factors are not necessarily in tandem with the nucleic acid sequence encoding the polypeptide.

An activator is a protein, which activates transcription of a nucleic acid sequence encoding a polypeptide (Kudla et al., 1990, *EMBO Journal* 9:1355-1364; Jarai and Buxton, 1994, *Current Genetics* 26:2238-244; Verdier, 1990, *Yeast* 6:271-297). The nucleic acid sequence encoding an activator may be obtained from the genes encoding *Bacillus stearothermophilus* NprA (nprA), *Saccharomyces cerevisiae* heme activator protein 1 (hap1), *Saccharomyces cerevisiae* galactose metabolizing protein 4 (gal4), and *Aspergillus nidulans* ammonia regulation protein (areA), and *A. oryzae* amyR. For further examples, see Verdier, 1990, supra and MacKenzie et al., 1993, *Journal of General Microbiology* 139: 2295-2307.

A chaperone is a protein, which assists another polypeptide in folding properly (Hartl et al., 1994, *TIBS* 19:20-25; Bergeron et al., 1994, *TIBS* 19:124-128; Demolder et al., 1994, *Journal of Biotechnology* 32:179-189; Craig, 1993, *Science* 260:1902-1903; Gething and Sambrook, 1992, *Nature* 355:33-45; Puig and Gilbert, 1994, *Journal of Biological Chemistry* 269:7764-7771; Wang and Tsou, 1993, *The FASEB Journal* 7:1515-11157; Robinson et al., 1994, *Bio/Technology* 1:381-384). The nucleic acid sequence encoding a chaperone may be obtained from the genes encoding *Bacillus subtilis* GroE proteins, *Aspergillus oryzae* protein disulphide isomerase, *Saccharomyces cerevisiae* calnexin, *Saccharomyces cerevisiae* BiP/GRP78, and *Saccharomyces cerevisiae* Hsp70. For further examples, see Gething and Sambrook et al, 1989, Molecular Cloning, A Laboratory Manual, 2d edition, Cold Spring Harbor, N.Y., and Hartl et al., 1994, *TIBS* 19:20-25.

A processing protease is a protease that cleaves a propeptide to generate a mature biochemically active polypeptide (Enderlin and Ogrydziak, 1994, *Yeast* 10:67-79; Fuller et al., 1989, *Proceedings of the National Academy of Sciences USA* 86:1434-1438; Julius et al., 1984, *Cell* 37:1075-1089; Julius et al., 1983, *Cell* 32:839-852). The nucleic acid sequence encoding a processing protease may be obtained from the genes encoding *Aspergillus niger* Kex2, *Saccharomyces cerevisiae* dipeptidylaminopeptidase, *Saccharomyces cerevisiae* Kex2, and *Yarrowia lipolytica* dibasic processing endoprotease (xpr6), tripeptidyl aminopeptidase (TPAP) (WO 96/14404), and the *A. oryzae* dipeptidyl aminopeptidase.

Regulatory Sequences

It may also be desirable to add regulatory sequences, which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems would include the lac, tac, and trp operator systems. In yeast, the ADH2 system or GAL1 system may be used. In filamentous fungi, the TAKA alpha-amylase promoter, *Aspergillus niger* glucoamylase promoter, and the *Aspergillus oryzae* glucoamylase promoter may be used as regulatory sequences. Other examples of regulatory sequences are those, which allow for gene amplification. In eukaryotic systems, these include the dihydrofolate reductase gene, which is amplified in the presence of methotrexate, and the metallothionein genes, which are amplified with heavy metals. In these cases, the nucleic acid sequence encoding the polypeptide would be placed in tandem with the regulatory sequence.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression, and possibly secretion.

The recombinant expression vector may be any vector (e.g., a plasmid or virus), which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids. The vector may be an autonomously replicating vector, i.e., a vector which exists as an extrachromosomal entity, the replication of which is independent of chromosomal replication, e.g., a plasmid, an extrachromosomal element, a minichromosome, a cosmid or an artificial chromosome. The vector may contain any means for assuring self-replication. Alternatively, the vector may be one which, when introduced into the host cell, is integrated into the genome and replicated together with the chromosome(s) into which it has been integrated. The vector system may be a single vector or plasmid or two or more vectors or plasmids which together contain the total DNA to be introduced into the genome of the host cell, or a transposon.

The vectors of the present invention preferably contain one or more selectable markers, which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. A frequently used mammalian marker is the dihydrofolate reductase gene. Suitable markers for yeast host cells are ADE2, HIS3, LEU2, LYS2, MET3, TRP1, and URA3. A selectable marker for use in a filamentous fungal host cell may be selected from the group including, but not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), tipC (anthranilate synthase), and glufosinate resistance markers, as well as equivalents from other species. Preferred for use in an *Aspergillus* cell are the amdS and pyrG markers of *Aspergillus nidulans* or *Aspergillus oryzae* and the bar marker of *Streptomyces hygroscopicus*. Furthermore, selection may be accomplished by co-transformation, e.g., as described in WO 91/17243, where the selectable marker is on a separate vector.

The vectors of the present invention preferably contain an element(s) that permits stable integration of the vector into the host cell genome or autonomous replication of the vector in the cell independent of the genome of the cell.

The vectors of the present invention may be integrated into the host cell genome when introduced into a host cell. For integration, the vector may rely on the nucleic acid sequence encoding the polypeptide or any other element of the vector for stable integration of the vector into the genome by homologous or none homologous recombination. Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination. These nucleic acid sequences may be any sequence that is homologous with a target sequence in the genome of the host cell, and, furthermore, may be non-encoding or encoding sequences.

For autonomous replication, the vector may further comprise an origin of replication enabling the vector to replicate autonomously in the host cell in question. Examples of bacterial origins of replication are the origins of replication of plasmids pBR322, pUC19, pACYC177, pACYC184, pUB110, pE194, pTA1060, and pAMβ1. Examples of origin of replications for use in a yeast host cell are the 2 micron origin of replication, the combination of CEN6 and ARS4, and the combination of CEN3 and ARS1. The origin of replication may be one having a mutation which makes its functioning temperature-sensitive in the host cell (see, e.g., Ehrlich, 1978, *Proceedings of the National Academy of Sciences USA* 75:1433).

For replication in fungi the episomal replicating AMA1 plasmid vector disclosed in WO 00/24883 may also be used.

More than one copy of a nucleic acid sequence encoding a polypeptide of the present invention may be inserted into the host cell to amplify expression of the nucleic acid sequence. Stable amplification of the nucleic acid sequence can be obtained by integrating at least one additional copy of the sequence into the host cell genome using methods well known in the art and selecting for transformants.

The procedures used to ligate the elements described above to construct the recombinant expression vectors of the present invention are well known to one skilled in the art (see, e.g., Sambrook et al, 1989, Molecular Cloning, A Laboratory Manual, 2d edition, Cold Spring Harbor, N.Y.).

Expression of an Anti-Microbial Polypeptide of the Invention

The present invention also relates to a method of homologous or heterologous production of an anti-microbial polypeptide of the invention in especially a bacteria or a fungal organism, especially a filamentous fungus.

More specifically the invention relates to a method of producing an anti-microbial polypeptide of the invention, in particular the amino acid sequence shown in SEQ ID NO: 2, or a fragment or a variant thereof. The method comprises the steps of:
(a) inserting a DNA construct encoding the anti-microbial polypeptide in question into a suitable expression vector,
(b) transforming a suitable host cell with the recombinant expression vector of step (a),
(c) culturing the transformed host cell in a suitable culture medium under conditions conducive to the production of the anti-microbial polypeptide, and
(d) recovering the polypeptide from the host cell or culture medium obtained in step (c).

In a preferred embodiment the DNA construct is a DNA construct of the invention, the expression vector is the vector of the invention, and/or the host cell is a host cell of the invention (all described further above).

In one embodiment the method of the invention comprises
(e) modifying the polypeptide, or fragment or variant obtained in step (d).

The invention also relates to a method of homologously or recombinantly producing an anti-microbial polypeptide of the invention, comprising cultivating a microorganism which, in nature, is capable of producing the polypeptide in question on a suitable culture medium and under conditions allowing the production of the polypeptide, and recovering the polypeptide from the resulting biomass and/or fermented culture medium.

The term "homologous" or "recombinant" expression or production means in the context of the present invention that the anti-microbial polypeptide in question is expressed from a gene endogenous to the donor cell or that a DNA construct comprising the gene encoding the anti-microbial polypeptide (AMP) in question is introduced into the donor cell and expressed from this genetically modified donor cell.

The term "donor cell" means the cell from which the gene encoding the anti-microbial polypeptide is obtained.

Contemplated donor microorganisms include micro-organisms such as bacteria, protozoae and algae, fungus, in particular yeasts and filamentous fungi. Especially contemplated are filamentous fungi of the genus *Aspergillus*, including *Aspergillus* species such as *A. pallidus, A. clavatus, A. longivesica, A. rhizopodus* and *A. clavatonanicus, A. giganteus*, and in particular of the group *A. Nigria*, including *Aspergillus niger, Aspergillus awamori, Aspergillus foetidus, Aspergillus japonicus, A. aculeatus, A. phoenicis, A. parasiticus,* and *A. saitoi.*

In the Example 1 cloning of a DNA sequence encoding an anti-microbial polypeptide is obtained from a specific strain of *A. niger*. However, it is to be understood that a number of type strain *A. niger* strain may be used as the donor cell. For instance, in Example 1 the polypeptide of the invention may be obtained from *A. niger* FGSC A798.

The invention also relates to a method of heterologous production a polypeptide exhibiting anti-microbial activity of the invention comprising (a) cultivating the host cell of the invention under conditions conducive to expression of the polypeptide; and (b) recovering the polypeptide.

Preferred host cells are disclosed above and include especially fungal organisms and bacteria, in particular filamentous fungi of the genus *Aspergillus*, more particularly of the group *A. Nigri*, including the species *A. niger* or the group *A. Flavus* including *A. oryzae*.

The host cell may also be a bacterium of the genus *Bacillus*.

The term "heterologous" expression or production means that the DNA construct comprising the gene encoding the anti-microbial polypeptide of the invention is introduced into a host cell, which is different from (i.e., not the same) as the donor cell. This means that producing an *A. niger* anti-microbial polypeptide recombinantly in another *Aspergillus niger* strain is considered to be heterologous expression or production.

The inventors have succeeded in heterologous production of the anti-microbial polypeptide of the invention in filamentous fungi of the genus *Aspergillus niger* and *A. oryzae*. When producing an anti-microbial polypeptide of the invention in a host cell of the genus *Aspergillus*, in particular of the group *Aspergillus Nigri* or *Aspergillus Flavus* high yields are obtained. For instance, in *A. niger* yields of secreted anti-microbial polypeptide (shown in SEQ ID NO: 2) as high as above 2.0 g/L was obtained (see Example 4).

Methods of Cloning the Anti-Microbial Polypeptide

Techniques used to isolate or clone a DNA sequence comprising an anti-microbial polypeptide are known in the art and include isolation from genomic DNA, preparation from cDNA, or a combination thereof.

The full-length gene encoding the anti-microbial polypeptide gene may for instance be cloned by what is referred to as "Expression Cloning" or by cloning techniques based on conserved regions.

Obtaining an Anti-Microbial Polypeptide of the Invention

The anti-microbial polypeptide of the invention may in a preferred embodiment be obtained from a filamentous fungus, in particular a strain of the genus *Aspergillus*, especially *A. niger*.

Expression Cloning

A number of expression cloning methods are known in the art including WO 99/32617. Another suitable example of such an Expression cloning method is described in WO 93/11249 (from Novo Nordisk), which is hereby incorporated by reference. The method comprises the steps of:
a) cloning, in suitable vectors, a DNA library from an organism suspected of producing one or more proteins of interest;
b) transforming suitable yeast host cells with said vectors;
c) culturing the host cells under suitable conditions to express any protein of interest encoding by a clone in the DNA library; and
d) screening for positive clones by determining any activity of a protein expressed in step c).

Conserved Region Cloning

The cloning of the DNA sequence (nucleic acid sequence) comprising an anti-microbial polypeptide gene from genomic DNA from a strain of, e.g., *Aspergillus niger*—or another organism as defined above—can be effected, e.g., by using the well-known polymerase chain reaction (PCR) or antibody screening of expression libraries to detect cloned DNA fragments with shared structural features. See, e.g., Innis et al., 1990, *A Guide to Methods and Application*, Academic Press, New York. Other nucleic acid amplification procedures such as ligase chain reaction (LCR), ligated activated transcription (LAT) and nucleic acid sequence-based amplification (NASBA) may be used.

The term "isolated" nucleic acid sequence as used herein refers to a nucleic acid sequence which is essentially free of other nucleic acid sequences, e.g., at least about 20% pure, preferably at least about 40% pure, more preferably about 60% pure, even more preferably about 80% pure, most preferably about 90% pure, and even most preferably about 95% pure, as determined by agarose gel electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment(s) comprising the nucleic acid sequence(s) from the target filamentous fungus, insertion of the fragment into a vector, and incorporation of the recombinant vector into a host cell where multiple copies or clones of the nucleic acid sequence will be replicated. The nucleic acid sequence may be of genomic, cDNA, RNA, semi-synthetic, synthetic origin, or any combinations thereof.

Cloning Based on Known Genes

Known genes encoding an anti-microbial polypeptides may be used to design an oligonucleotide probe, which can be used to isolate the full-length genes from other organisms. Further, such probes can also be used for hybridization with the genomic or cDNA of other anti-microbial polypeptide producing organism, following standard Southern blotting procedures, in order to identify and isolate the corresponding or related anti-microbial polypeptide encoding genes.

Probes for cloning the full-length genes can be considerably shorter than the entire sequence, but should be at least 15, preferably at least 25, and more preferably at least 40 nucleotides in length. Longer probes can also be used. Both DNA and RNA probes can be used. The probes are typically labeled for detecting the corresponding gene (for example, with $^{32}$P, $^{3}$H, $^{35}$S, biotin, or avidin). A PCR reaction using the degenerate primers mentioned herein and genomic DNA or first-strand cDNA from, e.g., the filamentous fungi of the genus *Aspergillus* and *Penicillium* can also can be used to generate a probe to clone the corresponding genomic or cDNA in other organims.

Composition of the Invention

The invention also relates to a composition comprising, as an active ingredient, an anti-microbial polypeptide of the invention as defined above, which further may comprise an additional biocidal agent.

Use of the Anti-Microbial Polypeptide of the Invention

The invention also relates to the use of an anti-microbial polypeptide or composition of the invention as a medicament. Further, an anti-microbial polypeptide or composition of the invention may also be used for the manufacture of a medicament for controlling or combating microorganisms, such as fungal organisms or bacteria.

The composition and anti-microbial polypeptide of the invention may be used as an anti-microbial veterinarian or human therapeutic or prophylactic agent. Thus, the composition and anti-microbial polypeptide of the invention may be used in the preparation of veterinarian or human therapeutic agents or prophylactic agents for the treatment of a microbial, such as fungal infection.

The composition of the invention comprises an effective amount of the anti-microbial polypeptide of the invention.

The term "effective amount" when used herein is intended to mean an amount of the anti-microbial polypeptide comprising the amino acid sequence shown in SEQ ID NO: 2, or a fragment or a variant thereof, which is sufficient to inhibit growth of the microorganisms in question.

Finally the invention also relates to wound healing composition or products such as bandages, medical devices such as, e.g., catheters and further to anti-dandruff hair products, such as shampoos.

Materials and Methods

Materials:
A. niger strain FGSC A798 from the Fungal Genetic Stock Center, U. of Kansas Medical Center.
A. niger MBin118 is A. niger, BO-1 (DSM 12665) (which is disclosed in WO 00/50576) derivative in which the alpha-amylase genes, the glucoamylase gene, the acid stable amylase gene and the prtT gene have been deleted.
Bech 2 is a cyclopiazonic acid (CPA) negative and kojic acid (KA) negative Aspergillus oryzae strain. The construction of Bech 2 is described in Example 1 of WO 00/39322.
pMT2188 is based on Aspergillus expression plasmid pCaHj527 (WO 0070064) constructed as described in Example 7 of Danish patent application PA 2001 00088 (published as WO 02/12472).

Methods:

Cultivation of an A. niger Strain Producing the Anti-Microbial Polypeptide

The production and subsequent purification of the anti-microbial polypeptide shown in SEQ ID NO: 1 may be carried out as described in WO 94/01459. In brief, the anti-microbial polypeptide is prepared as follows:

Cultivation on agar slants is carried out using an agar medium prepared from 39 g of Potato Dextrose Agar (from Difco) and distilled water up to 1000 ml. The agar slants are inoculated with the A. niger strain and grown for one week at 26° C.

Submerged Cultivation

A 500 ml Erlenmeyer flask containing 100 ml of AMC substrate (15 g meat extract, 20 g Peptone, 20 g corn starch, 5 g NaCl, 1 ml Pluronic, 1 liter $H_2O$) is inoculated with 5 ml of a spore suspension containing $10^6$ spores/ml prepared from an agar slant culture of A. niger obtained as described above containing $10^6$ spores per ml. The flask is shaken at 220 rpm at 30° C. for 3 days, after which the polypeptide can be recovered.

Isolation, Purification and Amino Acid Sequence Determination of the Anti-Microbial Polypeptide The fermentation broth obtained as described above is subjected to centrifugation, the mycelium is suspended in Tris-buffered saline at pH 7 and then subjected to a second centrifugation. The supernatants from the two centrifugations are combined and subjected to sterile filtration. The pH of the resulting supernatant preparation is adjusted to between 6.5 and 9 and the supernatant preparation is applied to a cation exchange resin (S Sepharose Fast Flow), which prior to application is equilibrated with a phosphate buffer at pH 6.5. Elution of active fractions from this resin is accomplished by the application of a buffer with a high ionic strength such as a buffer comprising 20 mM phosphate, 1.5 mM NaCl, pH 6.5. If necessary, the procedure is repeated after dilution with or dialysis against a buffer with ionic strength below or near that of 10 mM phosphate at pH 6.0. Elution from this second step is, if necessary, carried out as a gradient elution. The purity of the active fractions is assessed by HPLC.

The combined active fractions are subjected to sterile filtration on a 0.22 micro m filter (Millipore) prior to testing of the anti-microbial properties.

The purified Anti-microbial polypeptide is S-carboxymethylated using the method described by Nakaya et al. (1990), Eur. J. Biochem. 19, 31-38, and de-salted using reverse phase HPLC. The S-carboxymethylated anti-microbial polypeptide is subjected to N-terminal amino acid sequence determination on an Applied Biosystems 473A sequencer operated in accordance with the manufacturer's instructions.

Extinction Coefficient

The extinction coefficient of the anti-microbial polypeptide is estimated from the amino acid sequence shown in SEQ ID NO: 2 using the formula $$\varepsilon^{0.1\%}(280 \text{ nm}) = \frac{5690 \cdot (\text{No. Trp}) + 1280 \cdot (\text{No. Tyr}) + 120 \cdot (\text{No. Cys})}{\text{molecular mass}}$$

(Gill & von Hippel, 1989), where (No. Trp), (No. Tyr) and (No. Cys) are the number of Trp, Tyr and Cys residues in the amino acid sequence.

Based on this formula the extinction coefficient at 280 nm may be calculated. All polypeptide determinations are based on $OD_{280}$ measurements using this calculated extinction coefficient.

In vitro Analysis of Anti-Microbial Activity

The sensitivity of filamentous fungi and bacteria towards anti-microbial polypeptides may be tested using the below Bioassay I.

The petridishes used for assaying each of the bacteria and fungi are made from agar prepared as follows:

Aspergillus oryzae (26°C), Aspergillus niger (26° C.):

2-6 ml of a suspension prepared from an agar slant culture containing $10^6$ spores per ml are mixed with 100 ml of YPG-1-agar (yeast extract (0.4%), $KH_2PO_4$ (0.1%, $MgSO_4$, 7 $H_2O$, glucose (1.5%), Agar (1.5%), (48° C.).

Bacillus subtilis (30°C), Saccharomyces cerevicieae (26° C.):

A suspension prepared from an agar slant culture was suitably diluted so that a mixture of 6 ml of the diluted suspension and 100 ml of an Antibiotic medium-1 (Difco) (48° C.) contained $10^6$ spores per ml.

Bioassay I

The assay is carried out in petridishes (14 cm), each prepared from 35 ml of an agar suspension prepared as described above. In 4 mm holes made in the agar, 15 micro l of purified protein solution, the fermented broth and the sterile filtrate obtained as described above are applied. Plates containing bacteria are incubated for one day at the temperatures indicated in the list of bacteria. Plates containing fungi are incubated for two days at 26° C.

The inhibition zone (in mm) in the petridishes is used to quantitatively measure the activity of the polypeptide in question against selected fungi, yeasts and bacteria.

EXAMPLES

Example 1

Cloning of an A. niger Anti-Microbial Polypeptide Encoding Gene

Six degenerate primers were designed from the peptide sequence given by Lee et al (1999) Biochemical and Biophysical Research Communications, Vol. 263, No. 3, p.

646-651. The degeneration was used to cover most possibilities at the 3'end of the primers while the 5' is ends were chosen on the basis of *Aspergillus* codon use.

The three forward primers were made:

```
92: CCAAGTACGGYGGYGARTG,      (SEQ ID NO: 3)

93: CACAACACYTGYACYAAYTA,     (SEQ ID NO: 4)
and

94: AAGGAYGGYAAGAAYCAYGT.     (SEQ ID NO: 5)
```

The three reverse primers were made:

```
95: ACGGTCTTGTGRTGRTCRTC,     (SEQ ID NO: 6)

96: GTCGTCGTACTCRCARTGRTG,    (SEQ ID NO: 7)
and

97: GAGTGGTGGCGRTCRGTYTTRTG.  (SEQ ID NO: 8)
```

Chromosomal DNA was prepared from *Aspergillus niger* strain C-40-1. PCR with the nine relevant primer combinations were run on the four chromosomal DNAs. The PCR was run for 35 cycles and the experiment was run both with annealing temperature of 45° C. and of 50° C., i.e., a total of 72 PCR reactions.

The PCR products were separated on a 4% agarose gel. Due to the degenerate primers used, quite a few small PCR products had been generated in virtually all of the PCR reactions. Four potentially interesting band from *A. niger* C-40-1 PCRs were isolated and cloned into pCR4-TOPO T/A (purchased from Invitrogen, US). Particularly an approximately 190 bp fragment from the primer combination 93/95 and a 180 bp fragment from the combination 93/96 seemed promising. Sequencing of these pCR4 clones confirmed the two inserts to span a putative intron two. PCR amplification on genomic DNA from *Aspergillus niger* FGSC A798 using the 93/95 primer combination yielded a PCR fragment of identical length and sequence as that obtained with the strain C-40-1 genomic DNA.

The PCR93/95 insert was used as a probe in Southerns of *A. niger* C-40-1 genomic DNA. Not all digests appeared to be complete but the probe was definitely found to hybridize to a 1.8 kb Pst1 fragment, a 2.7 kb Hind3 fragment and a 4.8 kb EcoR1 fragment all of which were cloned by inverse PCR using primers from the originally cloned 190 bp fragment. These PCRs were done with the proofreading Expand PCR kit and the products were cloned into pCR4TOPOZeroBlunt (purchased from Invitrogen, US).

Example 2

Expression of the *A. niger* Anti-Microbial Polypeptide

The *A. niger* anti-microbial polypeptide was inserted in the *Aspergillus* expression vector pMT2188 to give pMT2446 (i.e., pMT2188 with an insert comprising the *A. niger* anti-microbial gene): pMT2446 was transformed into *A. oryzae* BECh2 (disclosed, e.g., on page 26 of WO 00/39322) and into *A. niger* MBin118. Thirty transformants of each strain were re-isolated twice under selective and non-inducing conditions on Cove minimal plates with sucrose and acetamide. To test expression of the anti-microbial polypeptide, transformants were grown for 6 days in tubes with 10 ml YPM (2% maltose). Supernatants were run on NuPage 10% Bis-Tris SDS gels with MES running buffer to allow separation in the low $m_w$ range.

It was noted that growth on YPM of several of the *A. oryzae* BECh2 transformants seemed inhibited while the *A. niger* MBin118 transformants seemed to grow normally.

Growth was inhibited in both *A. oryzae* BECh2 and *A. niger* MBin118 transformed with an expression plasmid for the *A. giganteus* anti-fungal polypeptide (AFP) disclosed in WO 94/01459).

Example 3

Purification and Characterisation of Anti-Microbial Peptide (AMP) from *Aspergillus niger* Strain MT2464

The broth from a fermentation of strain MT2464 (*A. niger* MBin118 carrying the pMT2446 plasmid) was centrifuged at 10000 rpm, 4° C. for 15 minutes. The supernatant was passed through a 0.22 micro m Durapore Membrane filter (Millipore). 1.0 L of 0.22 micro m filtered supernatant was added 5.0 L Milli-Q filtered $H_2O$ and adjusted to pH 6.0. The conductivity of the diluted supernatant was measured to 4.4 mSi/cm.

The diluted supernatant was loaded onto a 175 ml SP-Sepharose (Pharmacia Biotec) cat ion exchange column on a Pharmacia FPLC system and washed with a buffer A (10 mM $NaPO_4$, pH 6.0). Elution was performed by running a linear salt gradient obtained by mixing buffer A and B (10 mM $NaPO_4$, 1.0M NaCl pH 6.0) increasing the fraction of B from 0 to 100% over 7 column volumes. The flow rate was 10 ml/min. The MT2464-AMP eluted around 35% B. This purification resulted in a single band on SDS PAGE running around 7 kDa in agreement with the expected mass of the MT2464-AMP at 6511 Da.

N-Terminal Sequencing and Mass Spectrometry

The identity of the polypeptide product was confirmed by N-terminal sequencing.

10 microL sample was loaded directly onto a Micro TFA filter/Perkin Elmer that was placed in the cartridge of an Applied Biosystems Procise protein sequencer. The N-terminal sequencing was carried out using the method run file for Pulsed-Liquid. The following N-terminal sequence was obtained: LSKYGGECSVEHNT (SEQ ID NO: 9)

The sequence is identical to the expected N-terminal of MT2464-AMP.

Furthermore the mass of the purified MT2464-AMP was determined on a Voyager MALDI-TOF (Applied Biosystems) using alpha-Cyano-4-hydroxycinnamic acid as matrix. The mass was found to be 6511 Da as expected from the sequence.

Example 4

Fermentation of *A. niger* Transformant

Cultivation of Strain MT2467 (*A. niger* MBin118 Carrying the pMT2446 Plasmid)

Slant containing spores was used to inoculate a shake flask containing 200 mL MLC medium. The shake flask was placed in an incubator at 30° C./250 rpm for approximately 24 hours. After this point the content of the shake flask was pumped into a 2 L (working volume) fermentor. 44 hours after inoculation of the fermentor, addition of Feed medium was started, and during the rest of the cultivation, the feed rate was kept constant. The cultivation was run for a total of 165.8 hours, during which the last approx. 100 hours were characterized by a low oxygen tension and excess glucose in the fermentation broth.

| Cultivation conditions for cultivation AnAFP-02 | |
| --- | --- |
| Pre-culture medium | |
| Glucose * H$_2$O | 40 g/L |
| Soy meal | 50 g/L |
| Citric acid | 4 g/L |
| Pluronic PE6100 | 0.1 mL/L |
| Main Tank medium | |
| Glucose * H$_2$O | 100 g/L |
| (NH$_4$)$_2$HPO$_4$ (separate autoclavation) | 5.0 g/L |
| MgSO$_4$, 7H$_2$O | 2.0 g/L |
| KH$_2$PO$_4$ | 2.0 g/L |
| Trace metals | 0.25 mL/L |
| Pluronic | 1 mL/L |
| Feed medium | |
| Glucose * H$_2$O | 351 g/L |
| Pluronic | 2 mL/L |
| Other cultivation conditions | |
| Volume of medium in the batch phase | 2.0 L |
| Temperature | 34° C. |
| pH | 5.3 |
| Aeration | 2 L/min |
| Feed start criteria | 44 hours after inoculation |
| Feed rate | 10 g/hour | pH was regulated by adding 10% (w/w) NH$_3$ or 10% (w/w) H$_3$PO$_4$; the cultivation tanks were inoculated with the content of a 200 mL shake flask that had been incubated at 30□C for approximately 24 hours.

Determination of *A. niger* Anti-Microbial Polypeptide Yield Using the LC-MS Method Precise determination of the concentration of the purified MT2464-AMP was achieved by Amino acid analysis. A sample was hydrolysed by incubation in 6M HCl and 0.1% phenol under vacuum at 110° C. for 16 hours. The hydrolysate was analysed on a 420A amino acid analyzer (Applied Biosystems). The concentration of MT2464-AMP was determined to 8.15 mg/ml. This concentration was used as standard and used as basis for the LC-MS based quantification method.

Running the mass spectrometer, a Hewlett Packard 1100 series MSD, in the scan mode, a diluted sample from this standard gave one major peak. The mass spectrum of this peak showed five prominent ions, 931.2 Da, 1085.9 Da, 1303.2 Da, 1628.8 Da, and 2171.4 Da, which by deconvolution correspond to a peptide with a mass of 6510 Da. The quantification was carried out by selected ion monitoring (SIM mode) of the ions at 1086 Da, 1303 Da and 1629 Da. The column was a C4 Aquapore BU-300, 7 micro m, 30×3.2 mm from Perkin Elmer, and the eluents were A: 3% acetonitril and 0.1% trifluoroacetic acid; and B: 95% acetonitril and 0.085% trifluoroacetic acid. The flow rate was 0.25 mL pr. minute and a linear eluent gradient going from 0% to 50% B-eluent in 30 minutes was applied.

Figure 3:
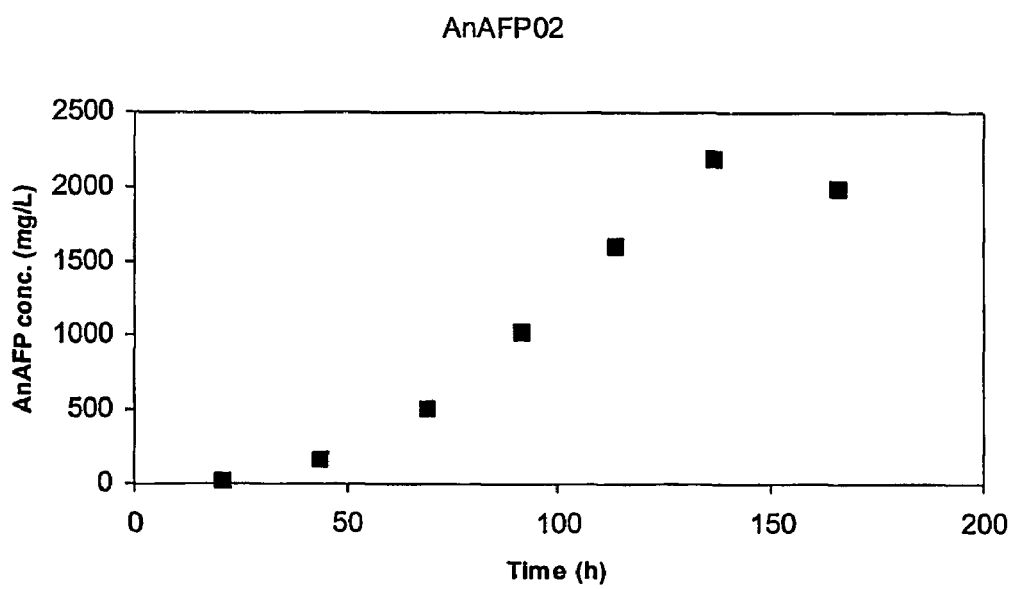
FIG. 3 shows the concentration of *Aspergillis niger* AMP during cultivation

A standard curve was made (see FIG. 2) and used to determine the concentration of the *A. niger* AMP (see FIG. 3). Based on this the *A. niger* anti-microbial polypeptide (AMP) yield was determined to be above 2.0 g/L.

SEQUENCE LISTING

```
<160> NUMBER OF SEQ ID NOS: 9

<210> SEQ ID NO 1
<211> LENGTH: 550
<212> TYPE: DNA
<213> ORGANISM: Aspergillus niger
<220> FEATURE:
<221> NAME/KEY: exon
<222> LOCATION: (106)..(225)
<220> FEATURE:
<221> NAME/KEY: sig_peptide
<222> LOCATION: (106)..(159)
<220> FEATURE:
<221> NAME/KEY: CDS
<222> LOCATION: (106)..(225)
<220> FEATURE:
<221> NAME/KEY: misc_feature
<222> LOCATION: (160)..(207)
<223> OTHER INFORMATION: Propeptide
<220> FEATURE:
<221> NAME/KEY: mat_peptide
<222> LOCATION: (208)..()
<220> FEATURE:
<221> NAME/KEY: Intron
<222> LOCATION: (226)..(293)
<220> FEATURE:
<221> NAME/KEY: exon
<222> LOCATION: (294)..(380)
<220> FEATURE:
<221> NAME/KEY: CDS
<222> LOCATION: (294)..(380)
<220> FEATURE:
<221> NAME/KEY: Intron
<222> LOCATION: (381)..(441)
<220> FEATURE:
<221> NAME/KEY: exon
```

```
<222> LOCATION: (442)..(510)
<220> FEATURE:
<221> NAME/KEY: CDS
<222> LOCATION: (442)..(510)

<400> SEQUENCE: 1
ccacggcgct ccaatccaca agatatcaat ctcaccagct caacaaattt cctctctctt      60
aactactcta caccaccgca acttccacaa aactacatcc tcaaa atg cag ctc acc     117
                                                  Met Gln Leu Thr agc att gcc atc atc ctc ttc gcc gca atg ggc gcc att gcc aat ccc       165
Ser Ile Ala Ile Ile Leu Phe Ala Ala Met Gly Ala Ile Ala Asn Pro
-30             -25                 -20                 -15 att gcg gcc gag gcg gac aat ctc gtt gct cgg gag gcg gag ctt agt       213
Ile Ala Ala Glu Ala Asp Asn Leu Val Ala Arg Glu Ala Glu Leu Ser
            -10                 -5                  -1   1 aaa tac gga gga gtaggtttcc tttcttccat gttctctatc gctgtagaga           265
Lys Tyr Gly Gly
        5 tggaactaac atatatgaac tataatag gaa tgc agc gtt gag cac aac acc        317
                              Glu Cys Ser Val Glu His Asn Thr
                                                  10 tgc aca tac cta aag ggc gga aag gat cac att gtc agt tgt cct tcg       365
Cys Thr Tyr Leu Lys Gly Gly Lys Asp His Ile Val Ser Cys Pro Ser
15              20              25                  30 gct gct aat ttg agg gtatattaag acttctgctt ctattctggt atgattgatc       420
Ala Ala Asn Leu Arg
            35 atgctaattt gttatctaca g tgc aag act gaa cgt cat cac tgc gaa tac       471
                       Cys Lys Thr Glu Arg His His Cys Glu Tyr
                                       40              45 gac gag cac cat aag acg gtc gat tgc cag act cct gtt tgattgggtt       520
Asp Glu His His Lys Thr Val Asp Cys Gln Thr Pro Val
                 50              55 gattcggttt cacagggaca taggccaatt                                      550

<210> SEQ ID NO 2
<211> LENGTH: 92
<212> TYPE: PRT
<213> ORGANISM: Aspergillus niger

<400> SEQUENCE: 2

Met Gln Leu Thr Ser Ile Ala Ile Ile Leu Phe Ala Ala Met Gly Ala
                -30                 -25                 -20

Ile Ala Asn Pro Ile Ala Ala Glu Ala Asp Asn Leu Val Ala Arg Glu
            -15                 -10                 -5

Ala Glu Leu Ser Lys Tyr Gly Gly Glu Cys Ser Val Glu His Asn Thr
    -1   1              5                   10

Cys Thr Tyr Leu Lys Gly Gly Lys Asp His Ile Val Ser Cys Pro Ser
15              20                  25                  30

Ala Ala Asn Leu Arg Cys Lys Thr Glu Arg His His Cys Glu Tyr Asp
                35              40                  45

Glu His His Lys Thr Val Asp Cys Gln Thr Pro Val
            50                  55

<210> SEQ ID NO 3
<211> LENGTH: 19
<212> TYPE: DNA
<213> ORGANISM: Artificial Sequence
<220> FEATURE:
<223> OTHER INFORMATION: Primer
```

```
<220> FEATURE:
<221> NAME/KEY: misc_feature
<223> OTHER INFORMATION: Primer 92

<400> SEQUENCE: 3
ccaagtacgg yggygartg                                                    19

<210> SEQ ID NO 4
<211> LENGTH: 20
<212> TYPE: DNA
<213> ORGANISM: Aspergillus niger
<220> FEATURE:
<221> NAME/KEY: misc_feature
<223> OTHER INFORMATION: Primer 93

<400> SEQUENCE: 4
cacaacacyt gyacyaayta                                                   20

<210> SEQ ID NO 5
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Primer 94

<400> SEQUENCE: 5
cacaacacyt gyacyaayta                                                   20

<210> SEQ ID NO 6
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Primer 95

<400> SEQUENCE: 6
acggtcttgt grtgrtcrtc                                                   20

<210> SEQ ID NO 7
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Primer 96

<400> SEQUENCE: 7
gtcgtcgtac tcrcartgrt g                                                 21

<210> SEQ ID NO 8
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Primer 97

<400> SEQUENCE: 8
```

```
gagtggtggc grtcrgtytt rtg                                    23
```

<210> SEQ ID NO 9
<211> LENGTH: 14
<212> TYPE: PRT
<213> ORGANISM: Aspergillus niger
<220> FEATURE:
<221> NAME/KEY: MISC_FEATURE
<222> LOCATION: (1)..(14)
<223> OTHER INFORMATION: N-terminal

<400> SEQUENCE: 9

Leu Ser Lys Tyr Gly Gly Glu Cys Ser Val Glu His Asn Thr
1               5                   10

The invention claimed is:

1. An isolated polypeptide exhibiting anti-microbial activity, which
   (a) is encoded by a DNA sequence which is at least 95% identical to the part of SEQ ID NO:1 encoding the mature anti-microbial polypeptide, or
   (b) comprises the amino acid sequence from position 1 to position 58 shown in SEQ ID NO:2.

2. The polypeptide of claim 1, wherein the anti-microbial peptide has an N-terminal extension of 1-50 amino acids.

3. The polypeptide of claim 1, wherein the anti-microbial peptide has an N-terminal extension of 2-20 amino acids.

4. The polypeptide of claim 1, wherein the anti-microbial peptide has an N-terminal extension of 3-15 amino acids.

5. The polypeptide of claim 2, wherein the N-terminal extension does not contain an Arg (R).

6. The polypeptide of claim 2, wherein the N-terminal extension comprises a kex2 or kex2-like cleavage site.

7. The polypeptide of claim 2, wherein the N-terminal extension comprises at least two E and/or D amino acid residues.

8. The polypeptide of claim 2, wherein the N-terminal extension comprises one of the following sequences: EAE, EE, DE, DD.

9. The polypeptide according to claim 1, which is obtained from a microorganism.

10. The polypeptide of claim 9, wherein the polypeptide is obtained from *Aspergillus*.

11. The polypeptide of claim 10, wherein the polypeptide is obtained from *A. aculeatus, A. awamori, A. clavatonanicus, A. clavatus, A. foetidus, A. giganteus, A. japonicus, A. longivesica, A. niger, A. pallidus, A. parasiticus, A. phoenicis, A. rhizopodus,* and *A. saitoi*.

12. The polypeptide of claim 11, wherein the polypeptide is obtained from *A. niger*.

13. The polypeptide of claim 1, which comprises the amino acid sequence from position 1 to position 58 shown in SEQ ID NO: 2.

14. An anti-microbial composition comprising an anti-microbial polypeptide of claim 1 and an additional biocidal agent.

15. A method of controlling or combating microorganisms, comprising applying an anti-microbial polypeptide claim 1 to the microorganisms.

16. The polypeptide of claim 1, wherein the polypeptide is encoded by a DNA sequence which is at least 97% identical to the part of SEQ ID NO:1 encoding the mature anti-microbial polypeptide.

17. The polypeptide of claim 1, wherein the polypeptide is encoded by a DNA sequence which is at least 99% identical to the part of SEQ ID NO:1 encoding the mature anti-microbial polypeptide.

* * * * *

UNITED STATES PATENT AND TRADEMARK OFFICE
CERTIFICATE OF CORRECTION

PATENT NO. : 7,319,087 B2  Page 1 of 2
APPLICATION NO. : 10/474647
DATED : January 15, 2008
INVENTOR(S) : Morgens Trier Hansen It is certified that error appears in the above-identified patent and that said Letters Patent is hereby corrected as shown below:

Col. 31, line 13 at the end of the Sequence Listing, insert:
--

```
<210> 10
<211> 58
<212> PRT
<213> Aspergillus niger

<400> 10

Leu Ser Lys Tyr Gly Gly Glu Cys Ser Val Glu His Asn Thr Cys Thr
1               5                   10                  15

Tyr Leu Lys Gly Gly Lys Asp His Ile Val Ser Cys Pro Ser Ala Ala
            20                  25                  30

Asn Leu Arg Cys Lys Thr Glu Arg His His Cys Glu Tyr Asp Glu His
            35                  40                  45

His Lys Thr Val Asp Cys Gln Thr Pro Val
            50                  55

<210> 11
<211> 58
<212> PRT
<213> Aspergillus niger

<400> 11

Leu Ser Lys Tyr Gly Gly Glu Cys Ser Leu Glu His Asn Thr Cys Thr
1               5                   10                  15

Tyr Arg Lys Asp Gly Lys Asn His Val Val Ser Cys Pro Ser Ala Ala
            20                  25                  30
```

UNITED STATES PATENT AND TRADEMARK OFFICE
CERTIFICATE OF CORRECTION

PATENT NO. : 7,319,087 B2  
APPLICATION NO. : 10/474647  
DATED : January 15, 2008  
INVENTOR(S) : Morgens Trier Hansen Page 2 of 2

It is certified that error appears in the above-identified patent and that said Letters Patent is hereby corrected as shown below:

```
Asn Leu Arg Cys Lys Thr Asp Arg His His Cys Glu Tyr Asp Asp His
            35                  40                  45

His Lys Thr Val Asp Cys Gln Thr Pro Val
    50                  55

<210>  12
<211>  55
<212>  PRT
<213>  Aspergillus niger

<400>  12

Leu Ser Lys Tyr Gly Gly Glu Cys Ser Leu Glu His Asn Thr Cys Thr
1               5                   10                  15

Tyr Lys Gly Lys His Ile Val Ser Cys Pro Ser Ala Ala Asn Leu Arg
                20                  25                  30

Cys Lys Thr Asp Arg His His Cys Glu Tyr Asp Asp His His Lys Thr
            35                  40                  45

Val Asp Cys Gln Thr Pro Val
    50                  55
```
--

Signed and Sealed this

Twenty-seventh Day of January, 2009

JOHN DOLL  
*Acting Director of the United States Patent and Trademark Office*